United States Patent [19]

Haga et al.

[11] Patent Number: 4,783,451

[45] Date of Patent: * Nov. 8, 1988

[54] ORGANOPHOSPHORUS, COMPOUNDS AND INSECTICIDAL, MITICIDAL, NEMATICIDAL OR SOIL PESTICIDAL COMPOSITIONS CONTAINING THEM

[75] Inventors: Takahiro Haga, Kusatsu; Tadaaki Toki, Otsu; Toru Koyanagi, Kyoto; Hiroshi Okada, Kusatsu; Kiyomitsu Yoshida, Kusatsu; Osamu Imai, Kusatsu, all of Japan

[73] Assignee: Ishihara Sangyo Kaisha Ltd., Osaka, Japan

[ * ] Notice: The portion of the term of this patent subsequent to May 20, 2003 has been disclaimed.

[21] Appl. No.: 878,266

[22] Filed: Jun. 25, 1986

[30] Foreign Application Priority Data

Jun. 25, 1985 [JP] Japan ................... 60-138133
Jun. 27, 1985 [JP] Japan ................... 60-141352
Jun. 27, 1985 [JP] Japan ................... 60-141353
Nov. 5, 1985 [JP] Japan ................... 60-247470
Feb. 25, 1986 [JP] Japan ................... 61-039552

[51] Int. Cl.$^4$ .................. A01K 57/16; C07F 9/40
[52] U.S. Cl. ............... 514/92; 540/487; 544/54; 544/97; 548/243; 548/543; 548/111
[58] Field of Search ............ 514/92; 540/487; 544/54, 97; 546/21; 548/243, 543, 111

[56] References Cited

U.S. PATENT DOCUMENTS 3,433,798  3/1969  Bodde et al. ................ 548/21
4,590,182  5/1987  Haga et al. ................. 514/92
4,645,761  2/1987  Haga et al. ................. 548/111

FOREIGN PATENT DOCUMENTS 0146748  11/1984  European Pat. Off. ........ 314/92
2055816  7/1980  United Kingdom ............ 548/182

*Primary Examiner*—Robert T. Bond
*Attorney, Agent, or Firm*—Oblon, Fisher, Spivak, McClelland & Maier

[57] ABSTRACT

An organophosphorus compound having the formula:

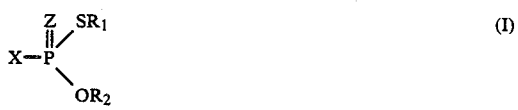

wherein X is

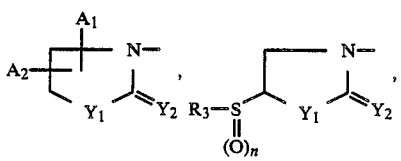

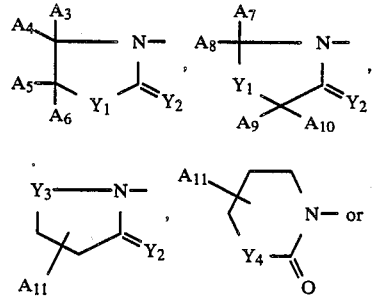

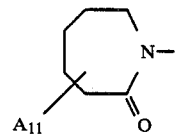

Z is an oxygen atom or a sulfur atom, and each of $R_1$ and $R_2$ is an alkyl group which may be substituted by halogen, alkoxy or alkylthio. The compound is useful as an insecticide, miticide, nematicide or soil pesticide.

31 Claims, No Drawings

ORGANOPHOSPHORUS, COMPOUNDS AND INSECTICIDAL, MITICIDAL, NEMATICIDAL OR SOIL PESTICIDAL COMPOSITIONS CONTAINING THEM

The present invention relates to novel organophosphorus compounds having insecticidal, miticidal, nematicidal and soil pesticidal activities. More particularly, the present invention relates to organophosphorus compounds with a phosphate compound bonded to the nitrogen atom of a substituted 2(or 4)-oxo(or thioxo)-oxa(or thia)zolidine ring, a substituted 3-oxo(or thioxo)-isoxa(or isothia)zolidine ring, a substituted 2-oxo-3,4,5,6-tetrahydro-1,3-oxa(or thia)zine ring or a substituted 2-oxo-piperidine(or hexahydroazepine) ring, or to the nitrogen atom at the 2-position of a substituted 3-oxo(or thioxo)-pyrazolidine ring, a process for their preparation, and insecticidal, miticidal, nematicidal or soil pesticidal compositions containing such compounds as active ingredients.

The organophosphorus compounds of the present invention with a phosphate compound bonded to the nitrogen atom of a certain specific heterocyclic ring having the nitrogen atom, are novel.

On the other hand, European Patent Publication No. 146,748 discloses phosphate compounds having a substituted 2-oxo(or thioxo)oxa(or thia)zolidine ring, and insecticidal, miticidal and nematicidal compositions containing them. However, the disclosed compounds are different in their chemical structure from the compounds of the present invention. Further, as will be seen in the Test Examples given hereinafter, the compounds of the present invention are highly effective against noxious insects, mites and nematodes.

The present invention provides novel organophosphorus compounds having the following formula, which include stereoisomers such as optical isomers:

$$\underset{X-P}{\overset{Z}{\underset{OR_2}{\|}}}\diagdown SR_1 \qquad (I)$$

wherein X is

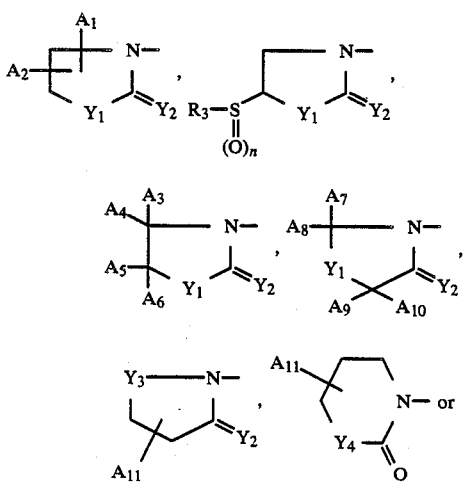

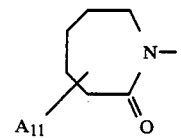

wherein each of $A_1$, $A_3$ and $A_5$ is a hydrogen atom or an alkyl group, $A_2$ is a thienyl group which may be substituted by halogen, or a phenyl group which is substituted by alkyl or alkoxy, each of $Y_1$ and $Y_2$ is an oxygen atom or a sulfur atom, $R_3$ is an alkyl group which may be substituted by halogen, a phenyl group which may be substituted by halogen, or —$CH_2CO_2R_4$ (wherein $R_4$ is an alkyl group), n is an integer of 0, 1 or 2, each of $A_4$ and $A_6$ is a hydrogen atom, a cyano group or —$CH_2Q$ (wherein Q is a phenylsulfinyl group, an alkylsulfonyloxy group, a dialkylamino group, an acyloxy group or a dialkoxydithiophosphono group), provided one of $A_4$ and $A_6$ is a cyano group or —$CH_2Q$,, each of $A_7$ to $A_{10}$ is a hydrogen atom, an alkyl group, an alkenyl group, a thienyl group which may be substituted by halogen, or a phenyl group which may be substituted by halogen, alkyl or alkoxy, $A_{11}$ is a hydrogen atom, an alkyl group or an alkoxycarbonyl group, $Y_3$ is an oxygen atom, $$\underset{-CH-}{\overset{R_5}{|}}$$

(wherein $R_5$ is a hydrogen atom, an alkyl group or —$CO_2R_7$ wherein $R_7$ is a hydrogen atom or an alkyl group) or $$\underset{-N-}{\overset{R_6}{|}}$$

(wherein $R_6$ is a phenyl group which may be substituted by halogen, alkyl or alkoxy), $Y_4$ is an oxygen atom, a sulfur atom or —$CH_2$—, Z is an oxygen atom or a sulfur atom, and each of $R_1$ and $R_2$ is an alkyl group which may be substituted by halogen, alkoxy or alkylthio.

The present invention also provides a process for preparing the compounds of the formula I, which comprises reacting a heterocyclic compound having the formula:

$$X-H \qquad (II)$$

wherein X is as defined above, with a phosphate compound having the formula:

$$\underset{Hal-P}{\overset{Z}{\underset{OR_2}{\|}}}\diagdown SR_1 \qquad (III)$$

wherein Hal is a halogen atom, and Z, $R_1$ and $R_2$ are as defined above, in the presence of an acid-acceptor.

Further, the present invention provides an insecticidal, miticidal, nematicidal or soil pesticidal composition comprising an insecticidally, miticidally, nematicidally or soil pesticidally effective amount of an organophosphorus compound of the formula I and, if necessary, a carrier.

Furthermore, the present invention provides an insecticidal, miticidal, nematicidal or soil pesticidal method, which comprises applying an insecticidally, miticidally, nematicidally or soil pesticidally effective amount of an organophosphorus compound of the formula I to a site to be protected from insects, mites, nematodes or soil pests.

Now, the present invention will be described in detail with reference to the preferred embodiments.

The alkyl group or the alkyl moiety included in $A_1$ to $A_{11}$, $R_3$ to $R_7$ and Q in X and $R_1$ and $R_2$ in the formula I, is preferably an alkyl group having from 1 to 6 carbon atoms such as methyl, ethyl, propyl, butyl, pentyl or hexyl. The alkenyl group included in $A_7$ to $A_{10}$ is preferably an alkenyl group having from 2 to 6 carbon atoms such as ethenyl, propenyl, butenyl, pentenyl or hexenyl. As the halogen atom included in $A_2$, $A_7$ to $A_{10}$, $R_1$ to $R_3$ and $R_6$, there may be mentioned fluorine, chlorine, bromine or iodine.

Among the substituents for $R_1$, an alkyl group is preferred. More preferred is an alkyl group having from 3 to 4 carbon atoms. Most preferred is n-propyl or sec-butyl.

Among the substituents for $R_2$, an alkyl group is preferred. More preferred is an alkyl group having from 1 or 2 carbon atoms. Most preferred is ethyl.

Among the substituents for Z, an oxygen atom is preferred.

Among the substituents for $A_7$ to $A_{10}$ in X, a hydrogen atom, an alkyl group, an alkenyl group or a phenyl group which may be substituted by halogen, alkyl or alkoxy, is preferred. Likewise, among the substituents for $Y_3$, —$CH_2$— or an oxygen atom is preferred. Further, among the substituents for $Y_2$ when X is

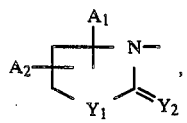

an oxygen atom is preferred.

The compounds of the formula I of the present invention may be prepared by e.g. the following processes:

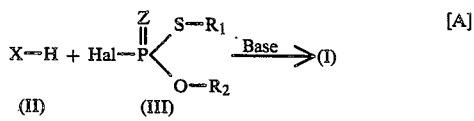

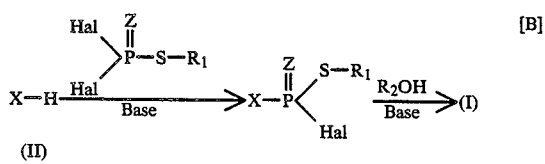

wherein Hal, Z, $R_1$ and $R_2$ are as defined above.

The above reaction is usually conducted within a temperature range of from $-100°$ to $50°$ C., preferably from $-80°$ C. to room temperature ($30°$ C.).

This reaction is conducted in the presence of an acid-acceptor. As the acid-acceptor, there may be mentioned an organic lithium compound such as n-butyl lithium, tert-butyl lithium or phenyl lithium; an inorganic base such as sodium hydroxide, potassium hydroxide, sodium hydride or potassium hydride; an organic base such as triethylamine or pyridine. Further, the reaction is preferably conducted in a solvent. As the solvent, there may be mentioned an aromatic hydrocarbon such as benzene, toluene, xylene or chlorobenzene; a cyclic or acyclic aliphatic hydrocarbon such as hexane or cyclohexane; an ether such as diethyl ether, methyl ethyl ether, dioxane or tetrahydrofuran; a nitrile such as acetonitrile, propionitrile or acrylonitrile; or an aprotic polar solvent such as dimethylformamide, dimethylsulfoxide, sulfolane or hexamethylphosphoric triamide.

The starting materials represented by the formula II include compounds having the following formulas II-1 to II-7:

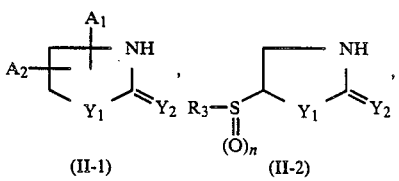

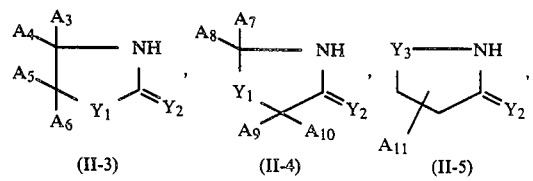

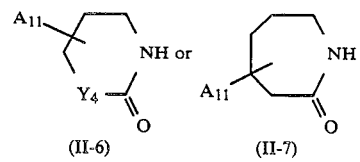

wherein $A_1$ to $A_{11}$, and $Y_1$ to $Y_4$ are as defined above. These compounds may be prepared by e.g. the following processes, respectively.

(1) Synthesis of compounds of the formula II-1

Substituted 2-oxo-thiazolidines may readily be prepared by the process disclosed in e.g. Japanese Unexamined Patent Publication Nos. 175180/1982, 29775/1983 or 29776/1983. Likewise, substituted 2-oxo-oxazolidines may readily be prepared by the process disclosed in Chemical Reviews, Vol. 67, p.197 (1967). Further, substituted 2-thioxo-oxa(or thia)zolidines may readily be prepared by reacting substituted 2-oxo-oxa(or thia)-zolidines with phosphorus pentasulfide.

(2) Synthesis of compounds of the formula II-2

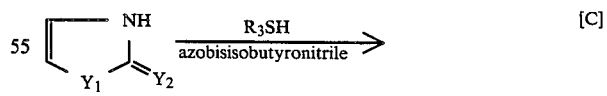

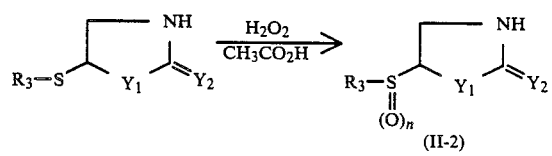

wherein $Y_1$, $Y_2$, $R_3$ and n are as defined above.

The compounds of the formula II-2 are novel compounds, and the chemical structures of the representative compounds will be given in Table 1.

TABLE 1

| Chemical structure | Physical properties (melting point °C.) |
|---|---|
| [C$_2$H$_5$S— structure with NH and O] | 82–86 |
| [sec-C$_4$H$_9$S— structure with NH and O] | 74–76 |
| [sec-C$_4$H$_9$S(O)$_2$— structure with NH and O] | 84–86 |

Among the compounds of the formula II-2, preferred are those wherein both $Y_1$ and $Y_2$ are oxygen atoms.

(3) Synthesis of compounds of the formula II-3

(a) Compounds wherein one of $A_3$ and $A_5$ is a hydrogen atom or an alkyl group, one of $A_4$ and $A_6$ is substituted by cyano, and $Y_1$ and $Y_2$ are oxygen atoms or sulfur atoms, may be readily prepared by the process disclosed in e.g. Journal of Organic Chemistry, Vol. 33, p.766 (1968).

(b) Compounds wherein one of $A_3$ and $A_5$ is a hydrogen atom or an alkyl group, one of $A_4$ and $A_6$ is —CH$_2$Q wherein Q is substituted by acyloxy or alkylsulfonyloxy, and $Y_1$ and $Y_2$ are oxygen atoms or sulfur atoms, may readily be prepared by reacting a compound wherein one of $A_4$ and $A_6$ is substituted by hydroxy methyl as disclosed in U.K. Patent No. 938,424, with a substituted sulfonyl chloride or an acyl chloride.

(c) Compounds wherein one of $A_3$ and $A_5$ is an oxygen atom or an alkyl group, one of $A_4$ and $A_6$ is —CH$_2$Q wherein Q is substituted by dialkylamino or dialkoxydithiophosphono, and $Y_1$ and $Y_2$ are oxygen atoms or sulfur atoms, may be readily obtained by reacting a compound wherein one of $A_4$ and $A_6$ is substituted by chloromethyl as disclosed in U.K. Patent No. 938,424, with an alkali metal salt of a substituted mercaptan or with a dialkylamine.

(d) Compounds wherein one of $A_3$ and $A_5$ is a hydrogen atom or an alkyl group, one of $A_4$ and $A_6$ is substituted by phenylsulfinyl, and $Y_1$ and $Y_2$ are oxygen atoms or sulfur atoms, may be readily prepared by oxidizing a known compound wherein one of $A_3$ and $A_5$ is an oxygen atom or an alkyl group, one of $A_4$ and $A_6$ is substituted by phenylsulfenyl, and $Y_1$ and $Y_2$ are oxygen atoms or sulfur atoms.

(4) Synthesis of compounds of the formula II-4

The compounds represented by the formula II-4 include compounds having the following formulas:

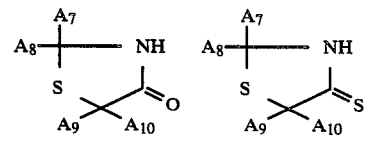

(II-4a)     (II-4b)

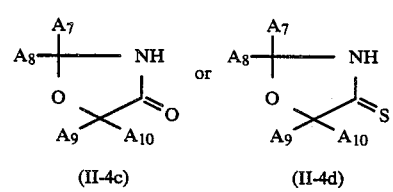

(II-4c)     (II-4d)

The compounds of the formulas II-4a to II-4d may be prepared, for instance, as follows:

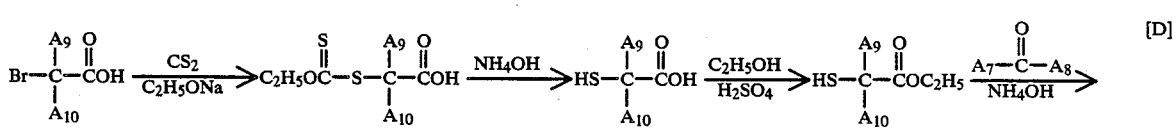

[D]

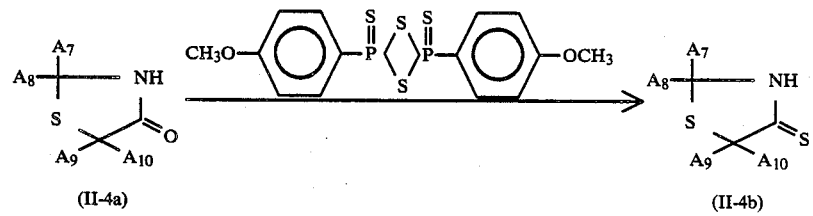

(II-4a)     (II-4b)

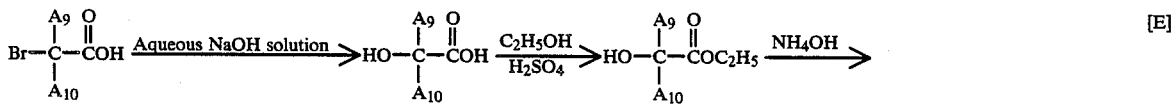

[E]

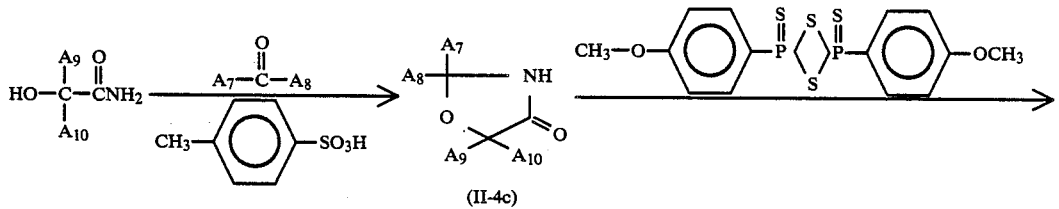

(II-4c)

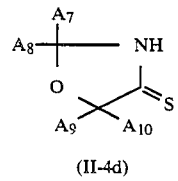

(II-4d)

The compounds of the formula II-4 are novel compounds, and the chemical structures of the representative compounds will be given in Table 2.

TABLE 2

| Chemical structure | Physical properties (melting point °C.) |
|---|---|
| (ring with N, O, C=O) | 84–86.5 |
| $CH_3$-substituted S,N,C=O ring | 52–61 |
| $C_2H_5$-substituted S,N,C=O ring | 73–76 |
| $n\text{-}C_3H_7$-substituted S,N,C=O ring | 77–80 |
| S,N,C=O ring with $CH_3$ | 65–85 |
| $CH_3$-substituted S,N,C=O ring | 68–77 |
| $CH_3OCH_2$-substituted S,N,C=O ring | 55.5–57 |
| Cl-phenyl substituted S,N,C=O ring | 162–166 |
| thienyl-substituted S,N,C=O ring | 138–140 |
| S,N,C=S ring | 124.5–126 |

Among the compounds of the formula II-4, preferred are those wherein $Y_1$ is a sulfur atom and $Y_2$ is an oxygen atom.

(5) Synthesis of compounds of the formulas II-5, II-6 and II-7

Compounds wherein $A_{11}$ is a hydrogen atom, may be prepared by e.g. the following processes.

2-Oxo-pyrrolidine can be prepared by the process disclosed in Berichte, Vol. 22, p. 3338; 2-thioxo-pyrrolidine may be prepared by the process disclosed in Berichte, Vol. 38, p. 1592; 3-oxo-isoxazolidine may be prepared by the process disclosed in Journal of the Chemical Society, Vol. 22, p. 76 (1957); 2-oxo-piperidine may be prepared by the process disclosed in Berichte, Vol. 21, p. 2240; 3-oxo-pyrazolidine may be prepared by the process disclosed in Chemical Abstract, Vol. 68, p. 68980d; 2-oxo-hexahydroazepin may be prepared by the process disclosed in Organic Synthesis Collective Volume, Vol. II, p. 371; 2-oxo-3,4,5,6-tetrahydro-1,3-oxazine may be prepared by the process disclosed in West German Patent No. 858,402; and 2-oxo-3,4,5,6-tetrahydro-1,3-thiazine may be prepared by the process disclosed in Japanese Unexamined Patent Publication Nos. 175180/1982, 29775/1983 or 29776/1983. Further, 3-thioxo-pyrazolidine and 3-thioxo-isoxazolidine, may be readily prepared by reacting 3-oxo-pyrazolidine and 3-oxo-isoxazolidine, with phosphorus pentasulfide.

Further, compounds wherein $A_{11}$ is an alkyl group or an alkoxycarbonyl group, may be readily prepared by introducing, by a usual method, the substituent to the compounds obtained by the above-mentioned processes.

The reaction conditions for the respective reactions for the preparation of the starting materials, such as the reaction temperature, the reaction time and the solvent or the base optionally employed, may suitably be selected from the reaction conditions for the conventional reactions of similar types.

Now, the present invention will be described in further detail with reference to Examples. However, it should be understood that the present invention is by no means restricted by these specific Examples.

Firstly, Synthetic Examples will be given.

SYNTHETIC EXAMPLE 1

Preparation of S-sec-butyl O-ethyl (5-ethylthio-2-oxo-3-oxazolidinyl)phosphonothiolate (Compound No. 5)

(1) A solution mixture comprising 3 g of 2-oxazolone, 25 ml of ethyl mercaptan and 600 mg of azobisisobutyronitrile, was reacted at 100° C. for 8 hours in an autoclave. After the completion of the reaction, excess ethyl mercaptan was distilled off, and the residue was purified by silica gel chromatography to obtain 1.6 g of 5-ethylthiooxazolidin-2-one having a melting point of from 82° to 86° C.

(2) 1.0 g of 5-ethylthiooxazolidin-2-one obtained in step (1), was dissolved in 30 ml of tetrahydrofuran, and then cooled to −78° C. Then, 4.8 ml of a hexane solution of n-butyllithium (1.55 M) was gradually dropwise added thereto, and the mixture was stirred for 15 minutes at the same temperature. Then, 10 ml of a tetrahydrofuran solution containing 1.8 g of S-sec-butyl O-ethyl phosphorochloridothiolate was gradually dropwise added thereto. The temperature of the solution was returned to room temperature, and the mixture was reacted for 2 hours. After the completion of the reaciton, the reaction solution was poured into ice water, and extracted with ethyl acetate. The extract layer was dried over anhydrous sodium sulfate, and the solvent was distilled off under reduced pressure. The residue was purified by silica gel column chromatography to obtain 1.1 g of S-sec-butyl O-ethyl (5-ethylthio-2-oxo-3-oxazolidinyl) phosphonothiolate having a refractive index ($n_D^{18.6}$) of 1.5128.

SYNTHETIC EXAMPLE 2

Preparation of S-sec-butyl O-ethyl (2-methyl-4-oxo-3-thiazolidinyl)phosphonothiolate (Compound No. 23)

(1) A solution prepared by dissolving 3.0 g of acetaldehyde in 10 ml of ethanol, was dropwise added to 8.5 g of 28% aqueous ammonia at room temperature, and the mixture was stirred for 1 hour. Then, a solution prepared by dissolving 8.0 g of ethyl thioglycolate in 10 ml of ethanol, was dropwise added at room temperature under stirring, and then the reaction was continued at room temperature for 4.5 hours.

After the completion of the reaction, the solvent was distilled off under reduced pressure, and the residue was purified by silica gel column chromatography to obtain 7.3 g of 2-methyl-4-oxothiazolidine having a melting point of from 52° to 61° C.

(2) 0.68 g of 2-methyl-4-oxothiazolidine obtained in step (1) was dissolved in 25 ml of dried tetrahydrofuran, and 0.28 g of 60% sodium hydride was added at 10° C. Then, the reaction solution was returned to room temperature, and stirred for 1 hour. Then, the solution was cooled to 0° C., and a solution prepared by dissolving 1.38 g of S-sec-butyl O-ethyl phosphorochloridothiolate in 3 ml of tetrahydrofuran, was dropwise added at a temperature of from 0° to 5° C. After the dropwise addition, the mixture was returned to room temperature, and stirred for 3 hours to complete the reaction.

After the completion of the reaction, the reaction solution was poured into a dilute hydrochloric acid aqueous solution. After confirming that the reaction solution became acidic, the reaction solution was extracted twice with chloroform. The extract solution was neutralized by an aqueous sodium hydrogen carbonate, washed with water and then dried over anhydrous sodium sulfate. Then, the solvent was distilled off under reduced pressure. The residue thereby obtained, was purified by silica gel column chromatography to obtain 0.41 g of S-sec-butyl O-ethyl (2-methyl-4-oxo-3-thiazolidinyl)phosphonothiolate having a refractive index ($n_D^{21.8}$) of 1.5211.

SYNTHETIC EXAMPLE 3

Preparation of S-sec-butyl O-ethyl (4-oxo-3-oxazolidinyl)phosphonothiolate (Compound No. 30)

(1) To 6.5 g of 37% formalin, 4 g of glycol amide was added, and the mixture was stirred overnight at room temperature. Then, the reaction solvent was distilled off under reduced pressure, and dehydration and ring closure were conducted at 100° C./15 mmHg for 4 hours.

A distillate was obtained at a Kugel-Rohr temperature of 200° C./1 mmHg. The distillate was purified by silica gel column chromatography to obtain 1.7 g of 4-oxazolidinone having a melting point of from 84° to 86.5° C.

(2) 0.8 g of 4-oxo-oxazolidine obtained in step (1), was dissolved in 30 ml of dried tetrahydrofuran, and then 0.41 g of 60% sodium hydride was added at 10° C. Then, the reaction solution was returned to room temperature, and stirred for 1 hour. Then, the reaction solution was cooled to 0° C., and a solution prepared by dissolving 2.18 g of S-sec-butyl O-ethyl phosphorochloridothiolate in 3 ml of tetrahydrofuran, was dropwise added at a temperature of from 0° to 5° C. After the dropwise addition, the mixture was reacted at room temperature for 3 hours under stirring.

After the completion of the reaction, the reaction solution was poured into a dilute hydrochloric acid aqueous solution. After confirming that the reaction solution became acidic, the reaction solution was extracted twice with chloroform. The extract solution was neutralized by an aqueous sodium hydrogen carbonate solution, then washed with water and dried over anhydrous sodium sulfate. Then, the solvent was distilled off under reduced pressure. The residue thereby obtained, was purified by silica gel column chromatography to obtain 0.67 g of S-sec-butyl O-ethyl (4-oxo-3-oxazolidinyl)phosphonothiolate having a refractive index ($n_D^{20.3}$) of 1.4962.

SYNTHETIC EXAMPLE 4

Preparation of S-sec-butyl O-ethyl (5-cyano-2-oxo-3-oxazolidinyl)phosphonothiolate (Compound No. 20)

1.1 g of 5-cyanooxazolidin-2-one is dissolved in 30 ml of tetrahydrofuran, and cooled to −78° C. Then, 7 ml of a hexane solution of n-butyllithium (1.55 M) was gradually dropwise added thereto, and the stirring was continued at the same temperature for 15 minutes. Then, 2.4 g of S-sec-butyl O-ethyl phosphorochloridothiolate was gradually dropwise added thereto, and the mixture was reacted for 2 hours while returning the temperature to room temperature.

After the completion of the reaction, the reaction product was poured into ice water, and extracted by an addition of ethyl acetate. The extract layer was dried over anhydrous sodium sulfate. Then, solvent was distilled off, and the crude product thus obtained was purified by silica gel column chromatography to obtain 0.5 g of S-sec-butyl O-ethyl (5-cyano-2-oxo-3-oxazolidinyl)phosphonothiolate having a refractive index ($n_D^{25.4}$) of 1.4901.

SYNTHETIC EXAMPLE 5

Preparation of S-sec-butyl O-ethyl (tetrahydro-2-oxo-3-thiazinyl)phosphonothiolate (Compound No. 54)

1.7 g of tetrahydro-1,3-thiazin-2-one is dissolved in 30 ml of tetrahydrofuran, and then the solution was cooled to −78° C. Then, 11.2 ml of a hexane solution of n-butyllithium (1.55 M) was gradually dropwise added thereto, and stirring was continued at the same temperature for 15 minutes. Then, 10 ml of a tetrahydrofuran solution containing 3.5 g of S-sec-butyl O-ethyl phosphorochloridothiolate, was gradually dropwise added thereto, and the mixture was reacted for 2 hours while returning the temperature gradually to room temperature.

After the completion of the reaction, the reaction product was poured into ice water, and extracted with ethyl acetate. The extract layer was dried over anhydrous sodium sulfate, and the solvent was distilled off. The residue was purified by silica gel column chromatography to obtain 2.7 g of S-sec-butyl O-ethyl (tetrahydro-2-oxo-3-thiazinyl)phosphonothiolate having a refractive index ($n_D^{27.0}$) of 1.5315.

SYNTHETIC EXAMPLE 6

Preparation of S-sec-butyl O-ethyl (5-methyl-2-oxo-1-pyrrolidinyl)phosphonothiolate (Compound No. 48)

1.5 g of 5-methyl-2-oxo-pyrrolidine was dissolved in 15 ml of tetrahydrofuran, and the solution was cooled to −78° C. 9.7 ml of 1.55 M butyllithium (n-hexane solution) was dropwise added under stirring. Stirring was continued at the same temperature for 15 minutes, and then 3.9 g of S-sec-butyl O-ethyl phosphorochloridothiolate was dropwise added. Then, the temperature of the mixture was returned to room temperature, and the mixture was reacted for 3 hours.

After the completion of the reaction, the reaction product was poured into water, then extracted with ethyl acetate, and dried over anhydrous sodium sulfate. After drying, ethyl acetate was distilled off under reduced pressure, and the residue was purified by silica gel column chromatography to obtain 3.1 g of S-sec-butyl O-ethyl (5-methyl-2-oxo-1-pyrrolidinyl)phosphonothiolate having a refractive index ($n_D^{25.6}$) of 1.4940.

SYNTHETIC EXAMPLE 7

Preparation of S-sec-butyl O-ethyl (2-oxo-1-hexahydroazepinyl)phosphonothiolate (Compound No. 55)

1.0 g of s-caprolactam was dissolved in 10 ml of tetrahydrofuran, and the solution was cooled to −78° C. Then, 5.7 ml of 1.55 M butyllithium (n-hexane solution) was dropwise added. Then, the mixture was stirred at the same temperature for 15 minutes, and 2.1 g of S-sec-butyl O-ethyl phosphorochloridothiolate was dropwise added. The temperature of the mixture was returned to room temperature, and the mixture was stirred for 3 hours. Then, the reaction mixture was poured into an aqueous saturated sodium chloride solution, and extracted with ethyl acetate. The extract solution was dried over anhydrous sodium sulfate, and then the solvent was distilled off under reduced pressure. The residue was purified by silica gel column chromatography to obtain 0.42 g of S-sec-butyl O-ethyl (2-oxo-1-hexahydroazepinyl)phosphonothiolate having a refractive index ($n_D^{27.6}$) of 1.4978.

Representative specific compounds of the present invention will be presented in Table 3.

TABLE 3

$$\begin{array}{c} Z \quad S-R_1 \\ \parallel \diagup \\ X-P \\ \diagdown \\ O-R_2 \end{array} \quad (I)$$

| Compound No. | X | Z | R₁ | R₂ | Physical properties |
|---|---|---|---|---|---|
| 1 | 2-(CH₃)-phenyl-CH-S-C(=O)-N= | S | —n-$C_3H_7$ | —iso-$C_3H_7$ | Oily substance |
| 2 | 4-(CH₃O)-, 3-(CH₃)-phenyl-CH-S-C(=O)-N= | O | —n-$C_3H_7$ | —$C_2H_5$ | m.p. 128–132° C. |
| 3 | (3-methyl-thiophene)-CH-S-C(=O)-N= | O | —n-$C_3H_7$ | —$C_2H_5$ | $n_D^{26}$ 1.5238 |
| 4 | CH₃S-CH₂-O-C(=O)-N= | O | —sec-$C_4H_9$ | —$C_2H_5$ | $n_D^{17.8}$ 1.5182 |
| 5 | C₂H₅S-CH₂-O-C(=O)-N= | O | —sec-$C_4H_9$ | —$C_2H_5$ | $n_D^{18.6}$ 1.5128 |
| 6 | sec-C₄H₉S-CH₂-O-C(=O)-N= | O | —sec-$C_4H_9$ | —$C_2H_5$ | $n_D^{21.2}$ 1.5062 |

TABLE 3-continued $$\begin{array}{c} Z \\ \| \\ X-P \\ \diagdown O-R_2 \end{array} S-R_1 \quad (I)$$

| Compound No. | X | Z | $R_1$ | $R_2$ | Physical properties |
|---|---|---|---|---|---|
| 7 | PhS-CH(-)-CH2-N(C=O-O-) ring | O | —sec-$C_4H_9$ | —$C_2H_5$ | $n_D^{21.2}$ 1.5550 |
| 8 | $CH_3S$-CH(-)-CH2-N(C=O-O-) ring | O | —$C_2H_5$ | —sec-$C_4H_9$ | Oily substance |
| 9 | $CH_3OCCH_2S$(=O)- on oxazolidinone | O | —sec-$C_4H_9$ | —$C_2H_5$ | $n_D^{21.2}$ 1.5147 |
| 10 | $CH_3SO_2$- on oxazolidinone | O | —sec-$C_4H_9$ | —$C_2H_5$ | $n_D^{20.2}$ 1.4980 |
| 11 | $CH_3SO$- on oxazolidinone | S | —tert-$C_4H_9$ | —$CH_3$ | Oily substance |
| 12 | $CH_3CH_2CH(CH_3)$-$SO_2$- on oxazolidinone | O | —sec-$C_4H_9$ | —$C_2H_5$ | $n_D^{18.4}$ 1.5013 |
| 13 | Ph-$SOCH_2$- on oxazolidinone | O | —sec-$C_4H_9$ | —$C_2H_5$ | $n_D^{21.2}$ 1.5484 |
| 14 | $CH_3SO_2OCH_2$- on oxazolidinone | O | —sec-$C_4H_9$ | —$C_2H_5$ | $n_D^{25.0}$ 1.4962 |
| 15 | $CH_3SO_2OCH_2$- on oxazolidinone with $CH_3$ | O | —sec-$C_4H_9$ | —$C_2H_5$ | $n_D^{19.2}$ 1.5002 |
| 16 | Ph-N—N- on pyrazolidinone | O | —sec-$C_4H_9$ | —$C_2H_5$ | $n_D^{28.0}$ 1.5524 |
| 17 | $(C_2H_5)_2NCH_2$- on oxazolidinone | O | —sec-$C_4H_9$ | —$C_2H_5$ | $n_D^{27.6}$ 1.4860 |
| 18 | $CH_3COCH_2$-C($CH_3$)- on oxazolidinone | O | —sec-$C_4H_9$ | —$C_2H_5$ | $n_D^{19.4}$ 1.4880 |

TABLE 3-continued $$\begin{array}{c} Z \quad S-R_1 \\ \| \\ X-P \\ O-R_2 \end{array} \qquad (I)$$

| Compound No. | X | Z | R₁ | R₂ | Physical properties |
|---|---|---|---|---|---|
| 19 | (C₂H₅O)₂P(S)SCH₂-C(CH₃)-N= with -O-C(=O)- ring | O | —sec-C₄H₉ | —C₂H₅ | $n_D^{17.1}$ 1.5205 |
| 20 | NC-CH-N= with -O-C(=O)- ring | O | —sec-C₄H₉ | —C₂H₅ | $n_D^{25.4}$ 1.4901 |
| 21 | NC-CH-N= with -O-C(=O)- ring | S | —CH₃ | —n-C₃H₇ | Oily substance |
| 22 | S-CH₂-N= with -C(=O)- ring | O | —sec-C₄H₉ | —C₂H₅ | $n_D^{18.2}$ 1.5324 |
| 23 | CH₃-CH(S)-N= with -C(=O)- ring | O | —sec-C₄H₉ | —C₂H₅ | $n_D^{21.8}$ 1.5211 |
| 24 | C₂H₅-CH(S)-N= with -C(=O)- ring | O | —sec-C₄H₉ | —C₂H₅ | $n_D^{18.4}$ 1.5182 |
| 25 | n-C₃H₇-CH(S)-N= with -C(=O)- ring | O | —sec-C₄H₉ | —C₂H₅ | $n_D^{20.7}$ 1.5112 |
| 26 | n-C₃H₇-CH(S)-N= with -C(=O)- ring | O | —sec-C₄H₉ | —C₂H₅ | $n_D^{21.6}$ 1.5153 |
| 27 | (CH₃)₂C(S)-N= with -C(=O)- ring | O | —sec-C₄H₉ | —C₂H₅ | $n_D^{20.6}$ 1.5040 |
| 28 | S-CH₂-N= with -C(=O)- ring | O | —n-C₃H₇ | —C₂H₅ | $n_D^{20.7}$ 1.5418 |
| 29 | CH₃-CH(S)-N= with -C(=O)- ring | O | —n-C₃H₇ | —C₂H₅ | $n_D^{18.0}$ 1.5309 |
| 30 | O-CH₂-N= with -C(=O)- ring | O | —sec-C₄H₉ | —C₂H₅ | $n_D^{20.8}$ 1.4962 |
| 31 | S-CH(CH₃)-N= with -C(=O)- ring | O | —sec-C₄H₉ | —C₂H₅ | $n_D^{18.7}$ 1.5206 |

TABLE 3-continued

General formula (I):

$$X-P(=Z)(S-R_1)(O-R_2)$$

| Compound No. | X | Z | $R_1$ | $R_2$ | Physical properties |
|---|---|---|---|---|---|
| 32 | 2-methyl-thiazolidinone (CH₃ on ring carbon adj to S) — N-linked, ring: S-CH₂-C(=O)-N-CH(CH₃) | O | —n-C₃H₇ | —C₂H₅ | $n_D^{18.1}$ 1.5212 |
| 33 | thiazolidinone with CH₃ on carbon adj to N; ring: CH₃-CH(S)-CH₂-C(=O)-N— | O | —iso-C₄H₉ | —C₂H₅ | $n_D^{18.8}$ 1.5085 |
| 34 | thiazolidine-thione; ring: S-CH₂-C(=S)-N-CH₂— | O | —iso-C₄H₉ | —C₂H₅ | $n_D^{18.8}$ 1.5772 |
| 5 | 2-(2,4-dichlorophenyl)-thiazolidinone; ring: Ar-CH(S)-CH₂-C(=O)-N— | O | —sec-C₄H₉ | —sec-C₄H₉ | Oily substance |
| 36 | thiazolidine-thione; ring: S-CH₂-C(=S)-N-CH₂— | O | —sec-C₄H₉ | —C₂H₅ | $n_D^{18.2}$ 1.5820 |
| 37 | 2-phenyl-thiazolidinone; ring: Ph-CH(S)-CH₂-C(=O)-N— | O | —sec-C₄H₉ | —C₂H₅ | $n_D^{19.0}$ 1.5643 |
| 38 | 2-methyl-thiazolidinone; ring: CH₃-CH(S)-CH₂-C(=O)-N— | S | —sec-C₄H₉ | —C₂H₅ | Oily substance |
| 39 | thiazolidinone with CH₃ on C adj to C=O; ring: S-CH₂-CH(CH₃)-C(=O)-N-CH₂— | O | —C₂H₅ | —CH₃ | Oily substance |
| 40 | 2-ethyl-thiazolidinone; ring: C₂H₅-CH(S)-CH₂-C(=O)-N— | O | —n-C₃H₇ | —C₂H₅ | $n_D^{18.6}$ 1.5257 |
| 41 | 2-(methoxymethyl)-thiazolidinone; ring: CH₃OCH₂-CH(S)-CH₂-C(=O)-N— | O | —sec-C₄H₉ | —C₂H₅ | $n_D^{20.0}$ 1.5127 |
| 42 | 2-methyl-thiazolidinone with CH₃ on C adj to C=O; ring: CH₃-CH(S)-CH(CH₃)-C(=O)-N— | O | —sec-C₄H₉ | —C₂H₅ | $n_D^{18.6}$ 1.5144 |

TABLE 3-continued $$\begin{array}{c} Z \quad S-R_1 \\ \| \diagup \\ X-P \\ \diagdown \\ O-R_2 \end{array} \quad (I)$$

| Compound No. | X | Z | $R_1$ | $R_2$ | Physical properties |
|---|---|---|---|---|---|
| 43 | CH₃–CH(S–)–N(–)–C(=O)–CH(CH₃)– (ring) | O | —sec-$C_4H_9$ | —$C_2H_5$ | $n_D^{18.0}$ 1.5134 |
| 44 | CH₃–C(S–)(CH₃)–N(–)–C(=O)– (ring) | O | —sec-$C_4H_9$ | —$C_2H_5$ | Oily substance |
| 45 | 4-Cl-C₆H₄–CH(S–)–N(–)–C(=O)–CH₂– (ring) | O | —sec-$C_4H_9$ | —$C_2H_5$ | $n_D^{22.4}$ 1.5650 |
| 46 | 2-thienyl–CH(S–)–N(–)–C(=O)–CH₂– (ring) | O | —sec-$C_4H_9$ | —$C_2H_5$ | $n_D^{20.8}$ 1.5694 |
| 47 | 2-oxopyrrolidin-1-yl | O | —sec-$C_4H_9$ | —$C_2H_5$ | $n_D^{18.2}$ 1.5050 |
| 48 | 5-methyl-2-oxopyrrolidin-1-yl | O | —sec-$C_4H_9$ | —$C_2H_5$ | $n_D^{25.6}$ 1.4940 |
| 49 | 2-oxopiperidin-1-yl | O | —sec-$C_4H_9$ | —$C_2H_5$ | $n_D^{27.1}$ 1.5016 |
| 50 | 3-(ethoxycarbonyl)-2-oxopiperidin-1-yl | O | —sec-$C_4H_9$ | —$C_2H_5$ | Oily substance |
| 51 | 2-thioxopyrrolidin-1-yl | O | —n-$C_3H_7$ | —$C_2H_5$ | $n_D^{32.2}$ 1.5506 |
| 52 | 2,5-dioxopyrrolidin-1-yl | O | —sec-$C_4H_9$ | —$C_2H_5$ | $n_D^{17.8}$ 1.4928 |
| 53 | 2-oxo-1,3-oxazinan-3-yl | O | —sec-$C_4H_9$ | —$C_2H_5$ | $n_D^{17.0}$ 1.5055 |

TABLE 3-continued $$\begin{array}{c} Z \quad S-R_1 \\ \parallel \diagup \\ X-P \\ \diagdown \\ O-R_2 \end{array} \qquad (I)$$

| Compound No. | X | Z | R₁ | R₂ | Physical properties |
|---|---|---|---|---|---|
| 54 | (piperidine-2-thione-N-yl, S=C ring with S and C=O) | O | —sec-C₄H₉ | —C₂H₅ | $n_D^{27.0}$ 1.5315 |
| 55 | (7-membered lactam, N-yl with C=O) | O | —sec-C₄H₉ | —C₂H₅ | $n_D^{27.6}$ 1.4978 |
| 56 | (oxazolidinone, O—N ring with C=O) | O | —n-C₃H₇ | —C₂H₅ | $n_D^{15.7}$ 1.4940 |
| 57 | (pyrrolidinone with COCH₃ substituent, N-yl) | O | —sec-C₄H₉ | —C₂H₅ | $n_D^{19.4}$ 1.4980 |

Among the representative compounds listed in Table 3, Compounds Nos. 25 and 26, and Compounds Nos. 43 and 44, are diastereomers to each other, respectively. Further, Compound No. 42 is a mixture of Compounds Nos. 43 and 44.

The compounds of the present invention show excellent activities as active ingredients for insecticides, miticides, nematicides and soil pesticides. For instance, they are effective against plant parasitic mites such as two-spotted spider mite (*Tetranychus urticae*), carmine spider mite (*Tetranychus cinnabarinus*), citrus red mite (*Panonychus citri*) or bulb mite (*Rhizoglyphus echinopus*); agricultural insect pests such as diamondback moth (*Plutella xylostella*), cabbage armyworm (*Mamestra brassicae*), common cutworm (*Spodoptera litura*), colorado potato beetle (*Leptinotarsa decemlineata*), codling moth (*Laspeyresia pomonella*), bollworm (*Heliothis zea*), tobacco budworm (*Heliothis virescens*), boll weevil (*Anthonomus grandis*), gypsy moth (*Lymantria dispar*), cucurbit leaf beetle (*Aulacophora femoralis*), aphids, planthoppers, leafhoppers, scales, bugs, whiteflies, thrips, grasshoppers, anthomyiid flies, scarabs, black cutworm (*Agrotis ipsilon*), cutworm (*Agrotis segetum*) or ants; hygienic pests such as tropical rat mite (Ornithonyssus bacoti), cockroaches, housefly (*Musca domestica*) or house mosquito (*Culex pipiens pallens*); stored grain insect pests such as angoumois grain moth (*Sitotroqa cerealella*), azuki bean weevil (*Callosobruchus chinensis*), confused flour beetle (*Tribolium confusum*) or mealworms; household goods insect pests such as casemaking clothes moth (*Tinea pellionella*), black carpet beetle (*Anthrenus scrophularidae*) or subterranean termites; and other parasites on domestic animals such as fleas, lice or flies. Further, they are also effective against plant parasitic nematodes such as root-knot nematodes, cyst nematodes, root-lesion nematodes, rice white-tip nematode (*Aphelenchoides besseyi*), strawberry bud nematode (*Nothotylenchus acris*) or pine wood nematode (*Bursaphelenchus lignicolus*). Furthermore, they are effective also against the soil pests. The soil pests in the present invention are gastropods such as slugs or snails, or isopods such as pillbugs or sowbugs. Still further, they are effective also against mites having the resistance to dicofol and organophosphorus insecticides and against insect pests such as aphids and housefly having the resistance to organophosphorus insecticides. Moreover, the compounds of the present invention have excellent systemic properties, and by the application of the compounds of the present invention to soil treatment, not only noxious insects, noxious mites, noxious nematodes, noxious gastropods and noxious isopods in soil but also foliage pests can be controlled.

When used as active ingredients for insecticides, miticides, nematicides or soil pesticides, the compounds of the present invention may be formulated together with agricultural adjuvants into various forms such as dusts, granules, wettable powders, emulsifiable concentrates, dispersions, aerosols or pastes, just like conventional agricultural chemicals. When such formulations are to be actually used, they may be used as they are or after being diluted with suitable diluents such as water to a predetermined concentration.

Such formulations are usually composed of 0.5–90 parts by weight of active ingredient and 10–99.5 parts by weight of agricultural adjuvants.

As the agricultural adjuvants, there may be mentioned carriers, emulsifiers, suspending agents, dispersants, extenders, penetrating agents, wetting agents, thickeners or stabilizers. They may be added as the case requires. The carriers may be divided into solid carriers and liquid carriers. As the solid carriers, there may be mentioned powders of animal and plant origin, such as starch, activated carbon, soybean flour, wheat flour, wood powder, fish powder or powdered milk; or mineral powders such as talc, kaolin, bentonite, calcium carbonate, zeolite, diatomaceous earth, white carbon, clay, alumina or sulfur powder. As the liquid carriers, there may be mentioned water; alcohols such as methyl alcohol or ethylene glycol; ketones such as acetone or methyl ethyl ketone; ethers such as dioxane or tetrahydrofuran; aliphatic hydrocarbons such as kerosine or the like; aromatic hydrocarbons such as xylene, trimethylbenzene, tetramethylbenzene, cyclohexane or solvent naphtha; halogenated hydrocarbons such as chloroform or chlorobenzene; acid amides such as dimethylformamide; esters such as ethyl acetate or glycerine ester of a fatty acid; nitriles such as acetonitrile; or sulfur-containing compounds such as dimethyl sulfoxide.

Further, the compounds of the present invention may be used in combination with other agricultural chemicals such as insecticides, miticides, nematicides, fungicides, antiviral agents, attractants, herbicides or plant growth regulators, as the case requires. In some cases, the effectiveness will be improved by such combination.

For instance, as such insecticides, miticides or nematicides, there may be mentioned organophosphorus compounds such as O-(4-bromo-2-chlorophenyl) O-ethyl S-propyl phosphorothioate, 2,2-dichlorovinyl dimethyl phosphate, ethyl 3-methyl-4-(methylthio)phenyl isopropylphosphoramidate, O,O-dimethyl O-4-nitro-m-tolyl phosphorothioate, O-ethyl O-4-nitrophenyl phenylphosphonothioate, O,O-diethyl O-2-isopropyl-6-methylpyrimidin-4-yl phosphorothioate, O,O-dimethyl O-(3,5,6-trichloro-2-pyridyl) phosphorothioate, O,S-dimethyl acetylphosphoramidothioate or O-(2,4-dichlorophenyl) O-ethyl S-propyl phosphorodithioate; carbamate compounds such as 1-naphthyl methylcarbamate, 2-isopropoxyphenyl methylcarbamate, 2-methyl-2-(methylthio)propionaldehyde O-methylcarbamoyloxime, 2,3-dihydro-2,2-dimethylbenzofuran-7-yl methylcarbamate, dimethyl N,N'-[thiobis (methylimino)carbonyloxy] bisethanimidothioate, S-methyl N-(methylcarbamoyloxy) thioacetoimidate, N,N-dimethyl-2-methylcarbamoyloxyimino-2-(methylthio)acetamide, 2-(ethylthiomethyl)phenyl methylcarbamate, 2-dimethylamino-5,6-dimethylpyrimidin-4-yl dimethylcarbamate or S,S'-2-dimethyl aminotrimethylene bis(thiocarbamate); organic chlorine compounds such as 2,2,2-trichloro-1,1-bis(4-chlorophenyl)ethanol or 4-chlorophenyl-2,4,5-trichlorophenyl sulfone; organic metal compounds such as tricyclohexyltin hydroxide; pyrethroide compounds such as (RS)-α-cyano-3-phenoxybenzyl (RS)-2-(4-chlorophenyl)-3-methylbutyrate, 3-phenoxybenzyl (1RS)-cis,trans-3-(2,2-dichlorovinyl)-2,2-dimethylcyclopropanecarboxylate, (RS)-α-cyano-3-phenoxybenzyl (1RS)-cis,trans-3-(2,2-dichlorovinyl)-2,2-dimethylcyclopropanecarboxylate, (S)-α-cyano-3-phenoxybenzyl (1R)-cis-3-(2,2-dibromovinyl)-2,2-dimethylcyclopropanecarboxylate, (RS)-α-cyano-3-phenoxybenzyl (1RS)-cis,trans-3-(2-chloro-3,3,3-trifluoropropenyl)-2,2-dimethylcyclopropanecarboxylate or 4-methyl-2,3,5,6-tetrafluorobenzyl-3-(2-chloro-3,3,3-trifluoro-1-propene-1-yl)-2,2-dimethylcyclopropane carboxylate; benzoyl urea compounds such as 1-(4-chlorophenyl)-3-(2,6-difluorobenzoyl)urea, 1-[3,5-dichloro-4-(3-chloro-5-trifluoromethyl-2-pyridyloxy)-phenyl]-3-(2,6-difluorobenzoyl)urea or 1-(3,5-dichloro-2,4-difluorophenyl)-3-(2,6-difluorobenzoyl)urea; other compounds such as 2-tert-butylimino-3-isopropyl-5-phenyl-3,4,5,6-tetrahydro-2H-1,3,5,-thiadiazin-4-one, 3-(cyclohexylcarbamoyl)-trans-5-(4-chlorophenyl)-4-methyl-2-oxo-thiazolizine N-methylbis(2,4-xylyliminomethyl)amine or N'-(4-chloro-o-tolyl)-N,N-dimethylformamidine; juvenile hormone-like compounds such as isopropyl(2E,4E)-11-methoxy-3,7,11-trimethyl-2,4-dodecadienoate; and other compounds such as dinitro compounds, organic sulfur compounds, urea compounds or triazine compounds. Further, microbial insecticide such as *Bacillus thuringiensis* agent or nuclear polyhedrosis virus may also be used in combination with the compounds of the present invention.

As the fungicides, there may be mentioned organophosphorus compounds such as S-benzyl O,O-diisopropyl phosphorothioate, O-ethyl S,S-diphenyl phosphorodithioate or aluminium ethyl hydrogen phosphonate; organic chlorine compounds such as 4,5,6,7-tetrachlorophthalide or tetrachloroisophthalonitrile; dithiocarbamate compounds such as polymeric manganese ethylenebis(dithiocarbamate), polymeric zinc ethylenebis(dithiocarbamate), manganese ethylenebis(dithiocarbamate) complex with zinc salt, dizinc bis(dimethyldithiocarbamate)-ethylenebis(dithiocarbamate) or polymeric zinc propylenebis(dithiocarbamate); N-halogenothioalkyl compounds such as 3a,4,7,7a-tetrahydro-N-(trichloromethansulfenyl)phthalimide, 3a,4,7,7a-tetrahydro-N-(1,1,2,2-tetrachloroethansulfenyl)phthalimide, or N-(trichloromethylsulfenyl)phthalimide; dicarboxy imide compounds such as 3-(3,5-dichlorophenyl)-N-isopropyl-2,4-dioxoimidazolidine-1-carboxamide, (RS)-3-(3,5-dichlorophenyl)-5-methyl-5-vinyl-1,3-oxazolidine-2,4-dione or N-(3,5-dichlorophenyl)-1,2-dimethylcyclopropane-1,2-dicarboximide; benzimidazole compounds such as methyl 1-(butylcarbamoyl)benzimidazole-2-yl-carbamate or dimetyl 4,4'-(o-phenylene)bis(3-thioallophanate); azole compounds such as 1-(4-chlorophenoxy)-3,3-dimethyl-1-(1H-1,2,4-triazol-1-yl)butanone, 1-(biphenyl-4-yloxy)-3,3-dimethyl-1-(1H-1,2,4-triazol-1-yl) butan-2-ol, 1-[N-(4-chloro-2-trifluoromethylphenyl)-2-propoxyacetoimidoyl]imidazole, 1-[2-(2,4-dichlorophenyl)-4-ethyl-1, 3-dioxolan-2-ylmethyl]-1H-1,2,4-triazole, 1-[2-(2,4-dichlorophenyl)-4-propyl-1,3-dioxolan-2-ylmethyl]-1H-1,2,4-triazole or 1-[2-(2,4-dichlorophenyl)pentyl]-1H-1,2,4-triazole; carbinol compounds such as (±)-2,4'-dichloro-α-(pyrimidin-5-yl)benzhydryl alcohol or 2,4'-difluoro-α-(1H-1,2,4-triazol-1-ylmethyl) benzhydryl alcohol; benzanilide compounds such as 3'-isopropoxy-o-toluanilide or α,α,α-trifluoro-3'-isopropoxy-o-toluanilide; acylalanine compounds such as methyl N-(2-methoxyacetyl)-N-(2,6-xylyl)-DL-alaninate; pyridinamine compounds such as 3-chloro-N-(3-chloro-2,6-dinitro-4- α,α,α-trifluorotolyl)-5-trifluoromethyl-2-pyridinamine; and other compounds such as piperazine compounds, morpholine compounds, anthraquinone compounds, quinoxaline compounds, crotonic acid compounds, sulfenic acid compounds, urea compounds or antibiotic substances.

The insecticides, miticides, nematicides and soil pesticides of the present invention are effective for the control of various noxious soil insects, noxious mites, noxious nematodes and noxious pests. They are applied in an active ingredient concentration of from 1 to 20,000 ppm, preferably from 20 to 2,000 ppm. The active ingredient concentration may be optionally changed depending upon the formulation, the manner, purpose, timing or place of the application and the condition of the insect pests. For instance, aquatic noxious insects can be controlled by applying the formulation having the above-mentioned concentration to the site of the outbreak, and thus, the concentration of the active ingredient in water is less than the above-mentioned range.

The amount of the application of the active ingredient per unit surface area is usually from about 0.1 to 5,000 g, preferably from 10 to 1,000 g, per 10a. However, in a certain special case, the amount of the application may be outside the above range.

Various formulations containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a feed containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

Now, Test Examples of the present invention will be described.

The chemical structures of Comparative Compounds Nos. a to n are as follows:

a: 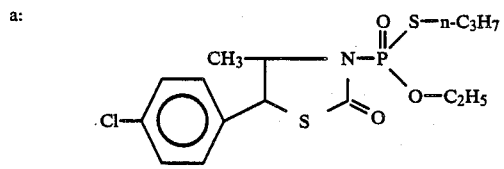

b: 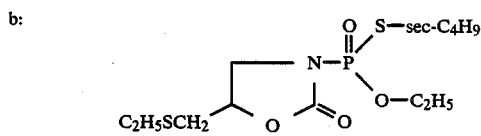

c: 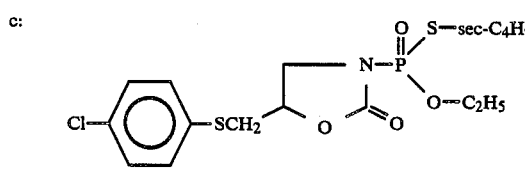

d: 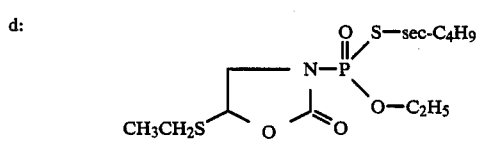

e: 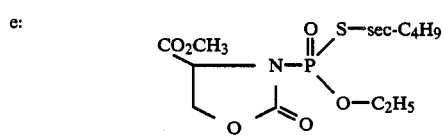

f: 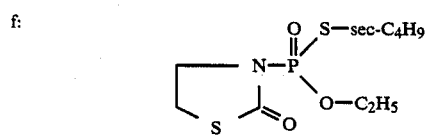

g: 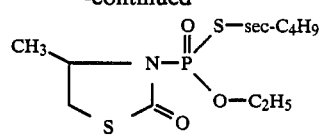

h: 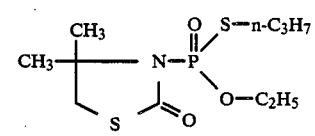

i: 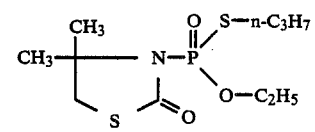

j: 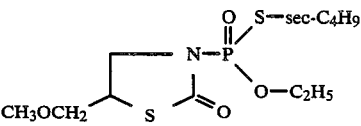

k: 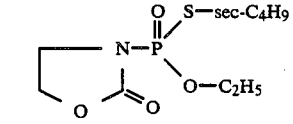

l: 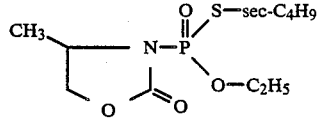

m: 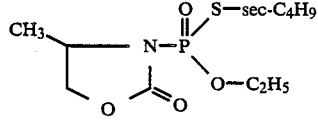

n: 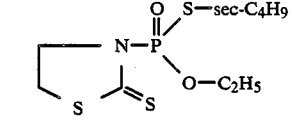

TEST EXAMPLE 1

Each of formulations containing the active ingredients (Compounds Nos. 1 to 58) was dispersed in water to obtain a dispersion of each active ingredient having a concentration of 800 ppm. Each of French bean seedlings with only one primary leaf left, was transplanted to a cup having a diameter of 7 cm and a height of 4 cm. About 30 nimphs and adults of two-spottend spider mite (*Tetranychus urticae*) were infested to the leaf of the French bean. Then, the French bean was dipped in the dispersion having the concentration of 800 ppm for about 10 seconds, then dried in air and kept in a constant temperature chamber with lightening at 26° C. At two days after the treatment, dead mites were counted, and the mortality was calculated by the following equation:

$$\text{Mortality (\%)} = \frac{\text{Number of dead mites}}{\text{Number of total mites}} \times 100$$

The mortality was more than 90% with respect to each of Compounds Nos. 1 to 57.

TEST EXAMPLE 2

Each of formulations containing the active ingredients identified in Table 3, was dispersed in water to obtain dispersions of each active ingredient having a concentration of 800 ppm. Leaves of cabbage were dipped in the respective dispersions for about 10 seconds, and then dried in air. A sheet of moistened filter paper was placed in a Petri dish having a diameter of 9 cm, and the dried leaves of cabbage were put on the filter paper. Larvae of diamondback moth (*Plutella xylostella*) in second or third instar were released on the leaves, and the Petri dishes were covered and kept in a constant temperature chamber with lightening at a temperature of 26° C. At two days after released, dead insects were counted, and the mortality was calculated by the following equation:

$$\text{Mortality (\%)} = \frac{\text{Number of dead insects}}{\text{Number of total insects}} \times 100$$

The mortality was more than 90% with respect to each of Compounds Nos. 1, 2, 4–7, 9, 10, 12–15, 18–20, 23–27, 29, 31–33, 37, 41, 47–49 and 52–54.

TEST EXAMPLE 3

The tests were conducted in the same manner as in Test Example 2 except that larvae of common cutworm (*Spodoptera litura*) in second or third instar were used instead of larvae of the diamondback moth in second or third instar, and the concentration of the active ingredient was changed from 800 ppm to 50 ppm. The results are shown in Table 4.

TABLE 4

| Compound No. | Mortality(%) 50 ppm | Comparative Compound No. | Mortality(%) 50 ppm |
|---|---|---|---|
| 1 | 100 | c | 50 |
| 19 | 100 | g | 20 |
| 41 | 90 | h | 0 |
| 57 | 100 | i | 10 |
|  |  | j | 20 |
|  |  | l | 50 |

TEST EXAMPLE 4

A rice seedling was dipped in a dispersion containing 50 ppm of each active ingredient for 10 seconds, then dried in air and put into a test tube with the root portion enclosed by absorbent cotton. Then, 10 adults of brown rice planthopper (*Nilaparvata lugens*) were released in the test tube, and the mouth of the test tube was covered with a gauze. Then, the test tube was kept in a constant temperature chamber with lightening at 26° C. At two days after the release, dead insects were counted, and the mortality was calculated in the same manner as in Test Example 2. The results are shown in Table 5.

TABLE 5

| Compound No. | Mortality (%) 50 ppm of active ingredient | Comparative Compound No. | Mortality (%) 50 ppm of active ingredient |
|---|---|---|---|
| 6 | 100 | a | 0 |
| 7 | 90 | b | 60 |
| 31 | 90 | f | 60 |
| 32 | 90 | i | 0 |
| 48 | 90 | k | 60 |

TABLE 5-continued

| Compound No. | Mortality (%) 50 ppm of active ingredient | Comparative Compound No. | Mortality (%) 50 ppm of active ingredient |
|---|---|---|---|
| 54 | 100 | n | 0 |

TEST EXAMPLE 5

The soil contaminated by southern root-knot nematode (*Meloidogyne incognita*) was put in a pot of 1/14,000a., and a dispersion containing an active ingredient was poured into the pot to bring the concentration of the active ingredient to 250 g/a. At two days after the treatment, the treated soil was mixed, and a tomato seedling in 3- or 4-leaf stage was transplanted in the pot. At twenty days after the treatment of the active ingredient, the root-gall index was investigated. The root-gall index was zero with respect to each of Compounds Nos. 1 to 57 The root-gall index was determined based on the following standards:

0: No galls
1: 1–25% of roots galled
2: 26–50% of roots galled
3: 51–75% of roots galled
4: 76–100% of roots galled

TEST EXAMPLE 6

Each of formulations containing active ingredients, was dispersed in water to obtain a dispersion of each active ingredient having a concentration of 800 ppm. Leaves of cabbage were dipped in the dispersion for about 10 seconds, and then dried in air. A sheet of moistened filter paper was placed in a Petri dish having a diameter of 9 cm, and the dried leaves of cabbage were put on the sheet. Apterous viviparous females of green peach aphid (*Myzus persicae*) were released on the leaves, and the Petri dish was covered and kept in a constant temperature chamber with lightening at 26° C. At two days after the release, dead insects were counted, and the mortality was calculated in the same manner as in Test Example 2. The mortality was more than 90% with respect to each of Compounds Nos. 1 to 57.

TEST EXAMPLE 7

Each of formulations containing the active ingredients identified in Table 6, was dispersed in water to obtain a dispersion of each active ingredient having a concentration of 50 ppm. Each of French bean seedlings with only one primary leaf left, was transplanted to a cup (same as Test Example 1), and about 30 nimphs and adults of two-spotted spider mite (*Tetranychus urticae*) having the resistance to dicofol and organophosphorus insecticides, were infested to the French bean. Then, the French bean was dipped in the dispersion having the above-mentioned predetermined concentration for about 10 seconds, then dried in air and kept in a constant temperature chamber with lightening at a temperature of 26° C. At two days after the treatment, the dead mites were counted, and the mortality was calculated in the same manner as in Test Example 1. The results are shown in Table 6.

TABLE 6

| Compound No. | Mortality (%) 50 ppm of active ingredient | Comparative Compound No. | Mortality (%) 50 ppm of active ingredient |
|---|---|---|---|
| 26 | 100 | b | 31 |
| 29 | 100 | d | 75 |
| 32 | 100 | e | 52 |
| 40 | 100 | j | 19 |
| 51 | 100 | m | 55 |
|  |  | Dicofol | 10 |
|  |  | ESP | 0 |

TEST EXAMPLE 8

Each of formulations containing the active ingredients identified in Table 3, was dispersed in water to obtain a dispersion containing 800 ppm of the active ingredient. Each of French bean seedlings having two primary leaves, was transplanted to a cup (same as the Test Example 1), and 10 ml of the dispersion having the above-mentioned concentration was applied by soil drenching. At two days after the treatment, about 30 nimphs and adults of two-spotted spider mite (*Tetranychus urticae*) having the resistance to dicofol and organophosphorus insecticides, were infested to the leaves, and the cup was kept in a constant temperature chamber with lightening at 26° C. At two days after infestation, the dead mites were counted, and the mortality was calculated in the same manner as in Test Example 1. The mortality was 100% with respect to each of Compounds Nos. 13, 22, 23, 28, 29, 32, 33, 41, 47–49, 51 and 53.

FORMULATION EXAMPLE 1

| (a) Compound No. 29 | 20 Parts by weight |
|---|---|
| (b) N,N'—dimethylformamide | 72 Parts by weight |
| (c) Polyoxyethylenealkylphenyl ether | 8 Parts by weight |

The above components are uniformly mixed and dissolved to obtain an emulsifiable concentrate.

FORMULATION EXAMPLE 2

| (a) Compound No. 48 | 50 Parts by weight |
|---|---|
| (b) Tetramethylbenzene | 38 Parts by weight |
| (c) An emulsifier mixture comprising an alkylbenzene sulfonate, a polyoxyethylenealkylphenol ether and a polyoxyethylenephenylphenol ether (Aglysol P-311 (Trade name), manufactured by Kao Soap Co. Ltd.) | 12 Parts by weight |

The above components are uniformly mixed and dissolved to obtain an emulsifiable concentrate.

FORMULATION EXAMPLE 3

| (a) Compound No. 15 | 85 Parts by weight |
|---|---|
| (b) The emulsifier mixture as used in Formulation Example 2 | 15 Parts by weight |

The above components are uniformly mixed to obtain a highly concentrated emulsifiable concentrate.

FORMULATION EXAMPLE 4

| (a) Compound No. 3 | 5 Parts by weight |
|---|---|
| (b) Talc | 95 Parts by weight |

The above components are uniformly mixed to obtain a dust.

FORMULATION EXAMPLE 5

| (a) Compound No. 51 | 5 Parts by weight |
|---|---|
| (b) Bentonite | 45 Parts by weight |
| (c) Kaoline | 50 Parts by weight |

The above components are kneaded together with a small amount of water, then extruded in a granular form and dried to obtain granules.

FORMULATION EXAMPLE 6

| (a) Compound No. 23 | 0.50 Part by weight |
|---|---|
| (b) Polyoxyethyleneoctylphenyl ether | 0.15 Part by weight |
| (c) Polyoxyethylene phosphate | 0.10 Part by weight |
| (d) Granular calcium carbonate | 99.25 Parts by weight |

Components (a) to (c) are preliminarily uniformly mixed, then diluted with a proper amount of acetone, and then sprayed on component (d), and then acetone was removed, to obtain granules.

FORMULATION EXAMPLE 7

| (a) Compound No. 33 | 50 Parts by weight |
|---|---|
| (b) Fine silica powder | 15 Parts by weight |
| (c) Fine clay powder | 25 Parts by weight |
| (d) A condensation product of sodium naphthalenesulfonate with formalin | 2 Parts by weight |
| (e) Dialkyl sulfosuccinate | 3 Parts by weight |
| (f) Polyoxyethylenealkylallyl ether sulfate | 5 Parts by weight |

The above components are uniformly pulverized and mixed to obtain a wettable powder.

FORMULATION EXAMPLE 8

| (a) Compound No. 54 | 5 Parts by weight |
|---|---|
| (b) Glycerin | 5 Parts by weight |
| (c) Milk powder | 3 Parts by weight |
| (d) Fish powder | 87 Parts by weight |

The above components are uniformly kneaded to obtain a paste.

FORMULATION EXAMPLE 9

| (a) Compound No. 3 | 10 Parts by weight |
|---|---|
| (b) Polyoxyethyleneoctylphenyl ether | 3 Parts by weight |
| (c) Kerosine | 87 Parts by weight |

The above components are uniformly mixed and dissolved to obtain an aerosol to be sprayed by compressed air.

FORMULATION EXAMPLE 10

| (a) Compound No. 6 | 5 Parts by weight |
|---|---|
| (b) An emulsifier mixture comprising a | 5 Parts by weight |

-continued

| | |
|---|---|
| polyethylene phenylphenol derivative, a polyethylene alkylaryl ether, a polyethylene sorbitan alkylate and an alkylaryl sulfonate (Sorpol 2806 (Trade name), manufactured by Toho Chemical Co. Ltd.) | |
| (c) Xylene | 90 Parts by weight |

The above components are uniformly mixed and dissolved to obtain an emulsifiable concentrate.

FORMULATION EXAMPLE 11

| | |
|---|---|
| (a) Compound No. 19 | 20 Parts by weight |
| (b) Dialkyl sulfosuccinate (Na salt) | 3 Parts by weight |
| (c) Polyoxyethylene octylphenyl ether | 6 Parts by weight |
| (d) Diatomacious earth (Granules) | 71 Parts by weight |

Components (a) to (c) are preliminarily uniformly mixed and sprayed on component (d) to obtain granules.

FORMULATION EXAMPLE 12

| | |
|---|---|
| (a) Compound No. 41 | 1 Part by weight |
| (b) Talc | 99 Parts by weight |

The above components are uniformly mixed to obtain a dust.

FORMULATION EXAMPLE 13

| | |
|---|---|
| (a) Compound No. 7 | 10 Parts by weight |
| (b) Fine silica powder | 5 Parts by weight |
| (c) Fine clay powder | 75 Parts by weight |
| (d) Sodium naphthalene sulfonate condensate with formaldehyde | 2 Parts by weight |
| (e) Dialkyl sulfosuccinate | 3 Parts by weight |
| (f) Polyoxyethylene alkylarylether sulfate | 5 Parts by weight |

The above components are uniformly pulverized and mixed to obtain a wettable powder.

We claim:

1. An organophosphorus compound having the formula:

$$X-P(=Z)(SR_1)(OR_2) \quad (I)$$

wherein X is

[structures with $A_1$, $A_2$, $Y_1$, $Y_2$, $R_3-S(O)_n-$, $A_3$-$A_6$, $A_7$-$A_{10}$, $A_{11}$, $Y_3$, $Y_4$ containing N-heterocyclic groups]

wherein each of $A_1$, $A_3$ and $A_5$ is a hydrogen atom or an alkyl group, $A_2$ is a thienyl group which may be substituted by halogen, or a phenyl group which is substituted by alkyl or alkoxy, each of $Y_1$ and $Y_2$ is an oxygen atom or a sulfur atom, $R_3$ is an alkyl group which may be substituted by halogen, a phenyl group which may be substituted by halogen, or —$CH_2CO_2R_4$ (wherein $R_4$ is an alkyl group), n is an integer of 0, 1 or 2, each of $A_4$ and $A_6$ is a hydrogen atom, a cyano group or —$CH_2Q$ (wherein Q is a phenylsulfinyl group, an alkylsulfonyloxy group, a dialkylamino group, an acyloxy group or a dialkoxydithiophosphono group), provided one of $A_4$ and $A_6$ is a cyano group or —$CH_2Q$, each of $A_7$ to $A_{10}$ is a hydrogen atom, an alkyl group, an alkenyl group, a methoxymethyl group, a thienyl group which may be substituted by halogen, or a phenyl group which may be substituted by halogen, alkyl or alkoxy, $A_{11}$ is a hydrogen atom, an alkyl group or an alkoxycarbonyl group, $Y_3$ is an oxygen atom, $$-\overset{R_5}{\underset{|}{C}}H-$$

(wherein $R_5$ is a hydrogen atom, an alkyl group or —$CO_2R_7$ wherein $R_7$ is a hydrogen atom or an alkyl group) or $$-\overset{R_6}{\underset{|}{N}}-$$

(wherein $R_6$ is a phenyl group which may be substituted by halogen, alkyl or alkoxy), $Y_4$ is an oxygen atom, a sulfur atom or —$CH_2$—, Z is an oxygen atom or a sulfur atom, and each of $R_1$ and $R_2$ is an alkyl group which may be substituted by halogen, alkoxy or alkylthio.

2. The compound according to claim 1, wherein Z is an oxygen atom.

3. The compound according to claim 1, wherein each of $R_1$ and $R_2$ is an alkyl group.

4. The compound according to claim 1, wherein $R_1$ is an alkyl group having 3 or 4 carbon atoms, and $R_2$ is an alkyl group having 1 or 2 carbon atoms.

5. The compound according to claim 1, wherein $R_1$ is a n-propyl group or a sec-butyl group, $R_2$ is an ethyl group, and Z is an oxygen atom.

6. The compound according to claim 5, wherein X is

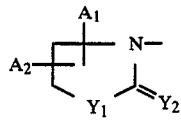

7. The compound according to claim 6, wherein $Y_2$ is an oxygen atom.

8. The compound according to claim 5, wherein X is

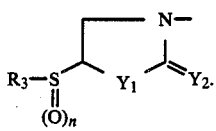

9. The compound according to claim 5, wherein X is

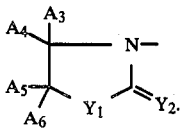

10. The compound according to claim 5, wherein X is

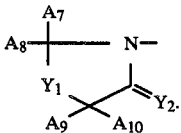

11. The compound according to claim 10, wherein each of $A_7$ to $A_{10}$ is a hydrogen atom, an alkyl group, an alkenyl group, or a phenyl group which may be substituted by halogen, alkyl or alkoxy.

12. The compound according to claim 5, wherein X is

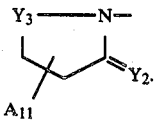

13. The compound according to claim 12, wherein $Y_3$ is an oxygen atom or —CH$_2$—.

14. The compound according to claim 5, wherein X is

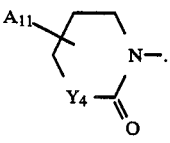

15. The compound according to claim 5, wherein X is

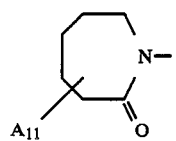

16. The compound according to claim 7, which is O-ethyl S-n-propyl [4-methyl-5-(2-thienyl)-2-oxo-3-thiazolidinyl]phosphonothiolate.

17. The compound according to claim 8, which is S-sec-butyl O-ethyl (5-methylsulfonyl-2-oxo-3-oxazolidinyl)phosphonothiolate.

18. The compound according to claim 9, which is S-sec-butyl O-ethyl (4-methyl-4-methylsulfonyloxymethyl-2-oxo-3-oxazolidinyl)phosphonothiolate.

19. The compound according to claim 11, which is S-sec-butyl O-ethyl (2-methyl-4-oxo-3-thiazolidinyl)-phosphonothiolate.

20. The compound according to claim 11, which is O-ethyl S-n-propyl (2-methyl-4-oxo-3-thiazolidinyl)-phosphonothiolate.

21. The compound according to claim 11, which is S-isobutyl O-ethyl (2-methyl-4-oxo-3-thiazolidinyl) phosphonothiolate.

22. The compound according to claim 13, which is S-sec-butyl O-ethyl (2-oxo-1-pyrrolidinyl) phosphonothiolate.

23. The compound according to claim 12, which is S-sec-butyl O-ethyl (5-methyl-2-oxo-1-pyrrolidinyl) phosphonothiolate.

24. The compound according to claim 13, which is O-ethyl S-n-propyl (2-thioxo-1-pyrrolidinyl) phosphonothiolate.

25. The compound according to claim 14, which is S-sec-butyl O-ethyl (tetrahydro-2-oxo-3-oxadinyl) phosphonothiolate.

26. The compound according to claim 15, which is S-sec-butyl O-ethyl (2-oxo-1-hexahydroazepinyl) phosphonothiolate.

27. The compound according to claim 13, which is S-sec-butyl O-ethyl (5-methoxycarbonyl-2-oxo-1-pyrrolidinyl)phosphonothiolate.

28. An insecticidal, miticidal, nematicidal or soil pesticidal composition comprising an insecticidally, miticidally, nematicidally or soil pesticidally effective amount of an organophosphorus compound of the formula I as defined in claim 1 and, if necessary, a carrier.

29. The composition according to claim 31, wherein the ratio of the organophosphorus compound to the carrier is from 0.5:99.5 to 90:10.

30. An insecticidal, miticidal, nematicial or soil pesticidal method, which comprises applying an insecticidally, miticidally, nematicidally or soil pesticidally effective amount of an organophosphorus compound of the formula I as defined in claim 1 to a site to be protected.

31. The method according to claim 30, wherein the organophosphorus compound is applied in an amount of from 0.1 to 5,000 g per 10 are.

* * * * *